United States Patent  
Pagano (10) Patent No.: US 7,641,664 B2
(45) Date of Patent: Jan. 5, 2010

(54) SURGICAL INSTRUMENTATION AND METHOD FOR TREATMENT OF A SPINAL STRUCTURE

(75) Inventor: Paul J. Pagano, Boardman, OH (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 709 days.

(21) Appl. No.: 10/778,650

(22) Filed: Feb. 12, 2004

(65) Prior Publication Data

US 2005/0182417 A1 Aug. 18, 2005

(51) Int. Cl.
*A61B 17/58* (2006.01)
*A61F 2/00* (2006.01)

(52) U.S. Cl. .......................................................... 606/92
(58) Field of Classification Search .................. 606/92, 606/94, 175, 182
See application file for complete search history.

(56) References Cited

U.S. PATENT DOCUMENTS

| | | | |
|---|---|---|---|
| 817,973 A | 4/1906 | Hausmann | 600/224 |
| 3,800,788 A | 4/1974 | White | |
| 3,850,176 A | 11/1974 | Gottschalk | |
| 3,875,595 A | 4/1975 | Froning | |
| 4,204,531 A | 5/1980 | Aginsky | 128/92 |
| 4,313,434 A | 2/1982 | Segal | |
| 4,323,071 A | 4/1982 | Simpson et al. | |
| 4,453,539 A | 6/1984 | Raftopoulos et al. | |
| 4,488,549 A | 12/1984 | Lee et al. | |
| 4,545,374 A | 10/1985 | Jacobson | |
| 4,592,749 A * | 6/1986 | Ebling et al. | 604/533 |
| 4,595,006 A | 6/1986 | Burke et al. | |
| 4,603,694 A | 8/1986 | Wheeler | |
| 4,625,722 A | 12/1986 | Murray | |
| 4,644,951 A | 2/1987 | Bays | |
| 4,706,670 A | 11/1987 | Andersen et al. | |
| 4,711,238 A * | 12/1987 | Cunningham | 606/79 |
| 4,714,478 A | 12/1987 | Fischer | |
| 4,854,312 A | 8/1989 | Raftopoulos et al. | 128/92 |
| 4,909,252 A | 3/1990 | Goldberger | |
| 4,969,888 A | 11/1990 | Scholten et al. | |

(Continued)

FOREIGN PATENT DOCUMENTS

DE 3736604 A1 5/1989

(Continued)

OTHER PUBLICATIONS

Walter Dick, Internal Fixation of Thoracic and Lumbar Spine Fractures, 1943, Hans Huber Publishers, 130 pages.

(Continued)

*Primary Examiner*—Anu Ramana
(74) *Attorney, Agent, or Firm*—Haynes and Boone, LLP (57) ABSTRACT

Instrumentation and method for treatment of a spinal structure, comprising an elongate member including a deformable distal portion having an initial configuration for placement within the spinal structure and a deformed configuration wherein the distal portion is outwardly deformed to form a cavity in the spinal structure. The elongate member comprises a cannula member and an actuator member that is removably positioned within the cannula member and configured to transition the deformable distal portion from the initial configuration toward the deformed configuration. The actuator member is selectively removed from the cannula member to provide a passageway for delivery of a material into the cavity formed in the spinal structure.

46 Claims, 6 Drawing Sheets

U.S. PATENT DOCUMENTS

| | | | |
|---|---|---|---|
| 4,990,148 A | 2/1991 | Worrick, III et al. | |
| 4,995,868 A | 2/1991 | Brazier | 604/105 |
| 5,015,255 A | 5/1991 | Kuslich | |
| 5,049,132 A | 9/1991 | Shaffer et al. | |
| 5,059,193 A | 10/1991 | Kuslich | 606/61 |
| 5,062,845 A | 11/1991 | Kuslich et al. | |
| 5,074,871 A | 12/1991 | Groshong | |
| 5,100,423 A | 3/1992 | Fearnot | |
| 5,102,413 A | 4/1992 | Poddar | |
| 5,108,404 A | 4/1992 | Scholten et al. | |
| 5,112,346 A | 5/1992 | Hiltebrandt et al. | |
| 5,171,278 A | 12/1992 | Pisharodi | 623/17 |
| 5,176,683 A | 1/1993 | Kimsey et al. | |
| 5,176,692 A | 1/1993 | Wilk et al. | |
| 5,197,971 A | 3/1993 | Bonutti | |
| 5,235,966 A | 8/1993 | Jamner | |
| 5,269,785 A | 12/1993 | Bonutti | |
| 5,290,306 A | 3/1994 | Trotta et al. | |
| 5,303,718 A | 4/1994 | Krajicek | |
| 5,330,429 A | 7/1994 | Noguchi et al. | |
| 5,331,975 A | 7/1994 | Bonutti | |
| 5,390,683 A | 2/1995 | Pisharodi | 128/898 |
| 5,423,850 A | 6/1995 | Berger | 606/192 |
| 5,431,676 A | 7/1995 | Dubrul et al. | |
| 5,445,639 A | 8/1995 | Kuslich et al. | |
| 5,454,365 A | 10/1995 | Bonutti | |
| 5,468,245 A | 11/1995 | Vargas | |
| 5,480,400 A | 1/1996 | Berger | 606/60 |
| 5,484,441 A | 1/1996 | Koros et al. | |
| 5,496,330 A | 3/1996 | Bates et al. | |
| 5,499,981 A | 3/1996 | Kordis | |
| 5,514,153 A | 5/1996 | Bonutti | |
| 5,522,790 A | 6/1996 | Moll et al. | |
| 5,522,846 A | 6/1996 | Bonutti | |
| 5,531,856 A | 7/1996 | Moll et al. | |
| 5,540,693 A | 7/1996 | Fisher | |
| 5,540,711 A | 7/1996 | Kieturakis et al. | |
| 5,549,679 A | 8/1996 | Kuslich | |
| 5,554,101 A | 9/1996 | Matula et al. | 600/214 |
| 5,562,736 A | 10/1996 | Ray et al. | |
| 5,620,458 A | 4/1997 | Green et al. | |
| 5,637,097 A | 6/1997 | Yoon | |
| 5,638,997 A | 6/1997 | Hawkins et al. | |
| D382,639 S * | 8/1997 | Musgrave et al. | D24/129 |
| 5,653,713 A | 8/1997 | Michelson | |
| 5,685,826 A | 11/1997 | Bonutti | 600/204 |
| 5,690,606 A | 11/1997 | Slotman | 600/206 |
| 5,693,100 A | 12/1997 | Pisharodi | 623/17 |
| 5,707,390 A | 1/1998 | Bonutti | 606/204 |
| 5,752,969 A * | 5/1998 | Cunci et al. | 606/167 |
| 5,755,732 A | 5/1998 | Green et al. | 606/170 |
| 5,772,681 A | 6/1998 | Leoni | |
| 5,782,713 A | 7/1998 | Yang | 474/160 |
| 5,782,747 A | 7/1998 | Zimmon | 600/104 |
| 5,785,647 A | 7/1998 | Tompkins et al. | 600/201 |
| 5,814,044 A | 9/1998 | Hooven | |
| 5,827,289 A | 10/1998 | Reiley et al. | 606/86 |
| 5,865,802 A | 2/1999 | Yoon et al. | 604/104 |
| 5,879,353 A | 3/1999 | Terry | |
| 5,882,340 A | 3/1999 | Yoon | 604/164 |
| 5,885,258 A | 3/1999 | Sachdeva et al. | |
| 5,913,867 A | 6/1999 | Dion | |
| 5,928,239 A * | 7/1999 | Mirza | 606/79 |
| 5,957,884 A | 9/1999 | Hooven | |
| 5,972,015 A | 10/1999 | Scribner et al. | 606/192 |
| 5,984,937 A | 11/1999 | Morse et al. | |
| 6,004,325 A * | 12/1999 | Vargas, III | 606/94 |
| 6,004,326 A | 12/1999 | Castro et al. | |
| 6,033,105 A | 3/2000 | Barker et al. | |
| 6,039,761 A | 3/2000 | Li et al. | 623/17 |
| 6,048,346 A | 4/2000 | Reiley et al. | |
| 6,066,154 A | 5/2000 | Reiley et al. | |
| 6,080,174 A | 6/2000 | Dubrul et al. | |
| 6,127,597 A | 10/2000 | Beyar et al. | 623/16 |
| 6,142,997 A | 11/2000 | Michelson | |
| 6,146,401 A | 11/2000 | Yoon et al. | 606/192 |
| 6,149,664 A | 11/2000 | Kurz | 606/194 |
| 6,187,015 B1 | 2/2001 | Brenneman | 606/108 |
| 6,190,381 B1 | 2/2001 | Olsen et al. | 606/32 |
| 6,200,320 B1 | 3/2001 | Michelson | |
| 6,214,016 B1 | 4/2001 | Williams et al. | 606/108 |
| 6,224,604 B1 | 5/2001 | Suddaby | |
| 6,228,022 B1 | 5/2001 | Friesem et al. | |
| 6,228,068 B1 | 5/2001 | Yoon | 604/246 |
| 6,228,082 B1 | 5/2001 | Baker et al. | 606/49 |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,280,456 B1 | 8/2001 | Scribner et al. | |
| 6,325,812 B1 | 12/2001 | Dubrul et al. | 606/185 |
| 6,379,364 B1 | 4/2002 | Brace et al. | |
| 6,383,188 B2 | 5/2002 | Kuslich et al. | |
| 6,395,007 B1 | 5/2002 | Bhatnagar et al. | |
| 6,423,083 B2 | 7/2002 | Reiley et al. | |
| 6,440,138 B1 | 8/2002 | Reiley et al. | |
| 6,468,279 B1 | 10/2002 | Reo | |
| 6,485,456 B1 | 11/2002 | Kletschka | |
| 6,530,933 B1 | 3/2003 | Yeung et al. | |
| 6,575,919 B1 | 6/2003 | Reiley et al. | |
| 6,575,978 B2 | 6/2003 | Peterson et al. | |
| 6,582,439 B1 | 6/2003 | Sproul | |
| 6,582,446 B1 | 6/2003 | Marchosky | |
| 6,599,291 B1 | 7/2003 | Foley et al. | |
| 6,607,544 B1 | 8/2003 | Boucher et al. | |
| 6,613,018 B2 | 9/2003 | Bagga et al. | |
| 6,613,054 B2 | 9/2003 | Scribner et al. | |
| 6,623,505 B2 | 9/2003 | Scribner et al. | |
| 6,626,905 B1 | 9/2003 | Schmiel et al. | |
| 6,632,197 B2 | 10/2003 | Lyon | |
| 6,641,587 B2 | 11/2003 | Scribner et al. | |
| 6,663,647 B2 | 12/2003 | Reiley et al. | |
| 6,676,665 B2 | 1/2004 | Foley et al. | |
| 6,679,886 B2 | 1/2004 | Weikel et al. | |
| 6,682,535 B2 | 1/2004 | Hoogland | |
| 6,716,216 B1 | 4/2004 | Boucher et al. | |
| 6,719,761 B1 | 4/2004 | Reiley et al. | |
| 6,719,773 B1 | 4/2004 | Boucher et al. | |
| 6,726,691 B2 | 4/2004 | Osorio et al. | |
| 6,730,095 B2 | 5/2004 | Olson, Jr. et al. | |
| 6,746,451 B2 * | 6/2004 | Middleton et al. | 606/79 |
| 6,814,734 B2 | 11/2004 | Chappuis et al. | |
| 6,899,719 B2 | 5/2005 | Reiley et al. | |
| 6,923,814 B1 | 8/2005 | Hildebrand et al. | |
| 6,979,341 B2 | 12/2005 | Scribner et al. | |
| 6,981,981 B2 | 1/2006 | Reiley et al. | |
| 7,081,122 B1 | 7/2006 | Reiley et al. | |
| 2001/0034526 A1 | 10/2001 | Kuslich et al. | |
| 2001/0034527 A1 | 10/2001 | Scribner et al. | |
| 2002/0010471 A1 | 1/2002 | Wironen et al. | |
| 2002/0013600 A1 | 1/2002 | Scribner et al. | |
| 2002/0020431 A1 | 2/2002 | Chou | |
| 2002/0022856 A1 | 2/2002 | Johnson et al. | |
| 2002/0026195 A1 | 2/2002 | Layne et al. | |
| 2002/0026197 A1 | 2/2002 | Foley et al. | |
| 2002/0068939 A1 | 6/2002 | Levy et al. | |
| 2002/0072768 A1 | 6/2002 | Ginn | 606/213 |
| 2002/0082605 A1 | 6/2002 | Reiley et al. | |
| 2002/0099385 A1 | 7/2002 | Ralph et al. | |
| 2002/0120240 A1 | 8/2002 | Bagga et al. | |
| 2002/0156483 A1 | 10/2002 | Voellmecke et al. | |
| 2002/0161373 A1 | 10/2002 | Osorio et al. | |
| 2002/0173796 A1 | 11/2002 | Cragg | |
| 2002/0173813 A1 | 11/2002 | Peterson et al. | |
| 2002/0188299 A1 | 12/2002 | Reiley et al. | |

| | | |
|---|---|---|
| 2002/0188300 A1 | 12/2002 | Arramon et al. |
| 2003/0004530 A1 | 1/2003 | Reo |
| 2003/0032963 A1 | 2/2003 | Reiss et al. |
| 2003/0036763 A1 | 2/2003 | Bhatnagar et al. |
| 2003/0078589 A1 | 4/2003 | Preissman |
| 2003/0125747 A1 | 7/2003 | Sproul |
| 2003/0144670 A1 | 7/2003 | Pavcnik et al. |
| 2003/0195518 A1 | 10/2003 | Cragg |
| 2003/0195547 A1 | 10/2003 | Scribner et al. |
| 2003/0220650 A1 | 11/2003 | Major et al. |
| 2003/0233096 A1 | 12/2003 | Osorio et al. |
| 2004/0002713 A1 | 1/2004 | Olson et al. |
| 2004/0024410 A1 | 2/2004 | Olson et al. |
| 2004/0052829 A1 | 3/2004 | Shimp |
| 2004/0064058 A1 | 4/2004 | McKay |
| 2004/0068264 A1 | 4/2004 | Treace |
| 2004/0068267 A1 | 4/2004 | Harvie et al. |
| 2004/0092946 A1 | 5/2004 | Bagga et al. |
| 2004/0102845 A1 | 5/2004 | Reynolds |
| 2004/0199170 A1 * | 10/2004 | Shiuzas et al. ............ 606/105 |

FOREIGN PATENT DOCUMENTS

| | | |
|---|---|---|
| DE | 390244 C2 | 5/2001 |
| EP | 1 293 228 A2 | 3/2003 |
| FR | 15864 | 5/1912 |
| GB | 512456 | 9/1939 |
| WO | WO 95/20362 | 8/1995 |
| WO | WO 96/39970 | 12/1996 |
| WO | WO 2004/049961 A1 | 6/2004 |
| WO | WO 2004049961 A1 * | 6/2004 |

OTHER PUBLICATIONS

H.G. Edeland, Open Reduction of Central Compression Fractures of the Tibial Plateau, Preliminary Report of a New Method and Device Arrangement, Department of Orthopaedic Surgery, Central Hospital, Molndal, Sweden, 1976, Acta orthop. scand. 47, 686-689.

N. Zemlyak, The Method of Endoprosthetic Replacement of the Coxofemoral Joint, Description of Invention (Supplement to the Certificate of Authorship), Apr. 12, 1983, SU 1148610A, U.S.S.R. State Committee on Inventions and Discoveries, 5 pages.

H. Daniaux, Transpedicular Repositioning and Spongiosaplasty in Fractures of Vertebral Bodies of the Lower Thoracic and Lumbar Spine (German), 1986, Unfallchirurg (Trauma Surgeon), University Clinic for Traumatologic Surgery, Innsbruck, 89:197-213, 17 pages.

H. Daniaux, Transpedicular Repositioning and Spongiosaplasty in Fractures of Vertebral Bodies of the Lower Thoracic and Lumbar Spine (English), 1986, Unfallchirurg (Trauma Surgeon), University Clinic for Traumatologic Surgery, Innsbruck, 89:197-213, 14 pages.

Nikolaus Nicola M.D. and Evaldo Lins M.D., Vertebral Hemangioma: Retrograde Embolization—Stabilization with Methyl Methacrylate, Department of Neurosurgery and Neuroradiology, University of Dusseldorf, Federal Republic of Germany, 1987, Elsevier Science Publishing Co., Inc., 27:481-6, 6 pages.

P. Galibert, H. Deramond, P. Rosat, D. Le Gars, Preliminary Note on Treatment of Spinal Angiomas by Percutaneous Acrylic Vertebroplasty (French and English), 1987, Masson, Paris, Neurosurgery Dept., Regional University Hospital Center, PO Box 3006, 80030 Amiens Cedex, France, 33:166-168, 5 pages.

C. Lapras, C. Mottolese, R. Deruty, Ch. Lapras Jr., J. Remond, J. Duquesnel, Percutaneous Injection of Methylmetacrylate in the Treatment of Severe Vertebral Osteoporosis and Osteolysis (P. Galibert Technique), 1989, Annales De Pediatrie, Paris Cedex, France, 43, 5, 371-376, 11 pages.

P. Galibert, H. Deramond, Percutaneous Acrylic Vertebroplasty as Treatment for Spinal Angiomas and Painful, Debilitating Spinal Conditions, 1990, Masson, Paris, 116, p. 326-335, 18 pages.

Dr. Matthias Richter-Turtur, Instrument for Treatment of Vertebral Fracture, Feb. 7, 1991, DE 39 22 044 A1, 9 pages.

H. Deramond, P. Galibert, C. Depriester-Debussche, Percutaneous Intraosseous Injections in Palliative Treatment of Bone Metastases, Amiens University Hospital Center, Place Victor-Pauchet, 80054 Amiens Cedex 1, France, p. 36-40, 9 pages.

Yves Bascoulergue MD, J. Duquesnel MD, R. Leclercq MD, C. Mottolese MD, C. Lapras MD, Percutaneous Injection of Methyl Methacrylate in the Vertebral Body for the Treatment of Various Diseases: Percutaneous Vertebroplasty, 1205, 1 page.

William R. Kennedy, M.D., Fractures of the Tibial Condyles a Preliminary Report on Supplementary Fixation With Methylmethacrylate, Clinical Orthopaedics and Related Research, Jul.-Aug. 1978, pp. 153-157, No. 134, J.B. Lippincott Company.

Sven Olerud, M.D. et al., Transpedicular Fixation of Thoracolumbar Vertebral Fractures, Clinical Orthopaedics and Related Research, Feb. 1988, pp. 44-51, No. 227.

Charles Rombold, M.D., Depressed Fractures of the Tibial Plateau, Treatment with Rigid Internal Fixation Early Mobilization, A Preliminary Report, The Journal of Bone and Joint Surgery, Jul. 1960, pp. 783-797, vol. 42-A No. 5.

Kevin D. Harrington, M.D. et al., The Use of Methylmethacrylate as an Adjunct in the Internal Fixation of Malignant Neoplastic Fractures, The Journal of Bone and Joint Surgery, Dec. 1972, pp. 1665-1676, vol. 54-A No. 8.

Howmedica, Inc., Exeter Pressurization System (Instructions), 1979, pp. 1-2.

* cited by examiner

SURGICAL INSTRUMENTATION AND METHOD FOR TREATMENT OF A SPINAL STRUCTURE

FIELD OF THE INVENTION

The present invention relates generally to the field of surgical instrumentation and methods for treatment of spinal structures, and more particularly relates to instrumentation and methods for reducing a vertebral compression fracture and fixation of the same.

BACKGROUND OF THE INVENTION

Various instruments and methods for the treatment of compression-type bone fractures and other osteoporotic and/or non-osteoporotic conditions have been developed. Such methods generally include a series of steps performed by a surgeon to correct and stabilize the compression fracture. An access opening is typically formed in the bone to be treated followed by the insertion of an inflatable balloon-like device through the access opening and into an interior portion of the bone. Inflation of the balloon-like device results in compaction of the cancellous bone and/or bone marrow against the inner cortical wall of the bone, thereby resulting in the formation of a cavity in the bone and reduction of the compression fracture. The balloon-like device is then deflated and removed from the bone. A biocompatible filling material such as methylmethacrylate cement or a synthetic bone substitute is sometimes delivered into the bone cavity and allowed to set to a hardened condition to provide internal structural support to the bone.

While the above-described instrumentation and methods provide an adequate protocol for the treatment and fixation of compression-type bone fractures, it has been found that the direction and magnitude of the force exerted by balloon-like devices is not sufficiently controllable. To the contrary, when such balloon-like devices are inflated, expansion occurs along a path of least resistance. As a result, the direction and magnitude of compaction of the cancellous bone and/or reduction of the compression fracture is uncontrolled and expansion occurs in multiple directions and along multiple axes with varying amounts of compaction force exerted onto the vertebral tissue. Additionally, previous instrumentation and methods for the treatment and fixation of compression-type bone fractures utilize separate instruments and devices to gain entry to the treatment site, to reduce the compression fracture, and/or to deliver filling material to the treatment site.

Thus, there is a general need in the industry to provide improved surgical instrumentation and methods for use in treatment of spinal structures than is currently available within the industry. The present invention meets this need and provides other benefits and advantages in a novel and unobvious manner.

SUMMARY OF THE INVENTION

The present invention relates generally instrumentation and methods for use in the treatment of spinal structures. While the actual nature of the invention covered herein can only be determined with reference to the claims appended hereto, certain forms of the invention that are characteristic of the preferred embodiments disclosed herein are described briefly as follows.

In one form of the present invention, instrumentation is provided for treatment of a spinal structure, comprising an elongate member including a deformable distal portion having an initial configuration for placement within a spinal structure and a deformed configuration wherein the distal portion is outwardly deformed to form a cavity in the spinal structure. The elongate member comprises a cannula member and an actuator member removably positioned within the cannula member and configured to transition the deformable distal portion from the initial configuration toward the deformed configuration. The actuator member is selectively removed from the cannula member to provide a passageway for delivery of a material into the cavity formed in the spinal structure.

In another form of the present invention, instrumentation is provided for treatment of a spinal structure, comprising a cannula member and an actuator member. The cannula member includes a distal portion and defines an axial passage and a transverse opening positioned adjacent the distal portion and communicating with the axial passage. The actuator member is removably positioned within the axial passage of the cannula member and includes a deformable portion positioned adjacent the transverse opening and being transitionable between an initial configuration for placement within a spinal structure and a deformed configuration defining at least one transverse projection extending through the transverse opening in the cannula member to form a cavity in the spinal structure. The actuator member is selectively removed from the cannula member to allow for the delivery of a material through the axial passage and into the cavity formed in the spinal structure.

In another form of the present invention, instrumentation is provided for treatment of a spinal structure, comprising an elongate member extending along a longitudinal axis and including a deformable distal portion having an initial configuration for insertion into a spinal structure and a mechanically deformed configuration for forming a cavity within the spinal structure. The instrumentation also includes means for mechanically deforming the distal portion from the initial configuration toward the mechanically deformed configuration to form the cavity in the spinal structure, and means for delivering a material through the elongate member and into the cavity in the spinal structure.

In another form of the present invention, a method is provided for treatment of the spine, comprising providing an instrument defining a cannula passage and including a deformable distal portion having an insertion configuration and a deformed configuration, positioning the distal portion of the instrument within a spinal structure while in the insertion configuration, transitioning the distal portion of the instrument toward the deformed configuration to form a cavity within the spinal structure, and delivering a material through the cannula passage and into the cavity in the spinal structure.

It is one object of the present invention to provide improved surgical instrumentation and methods for treatment of spinal structures.

Further objects, features, advantages, benefits, and aspects of the present invention will become apparent from the drawings and description contained herein.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 1:
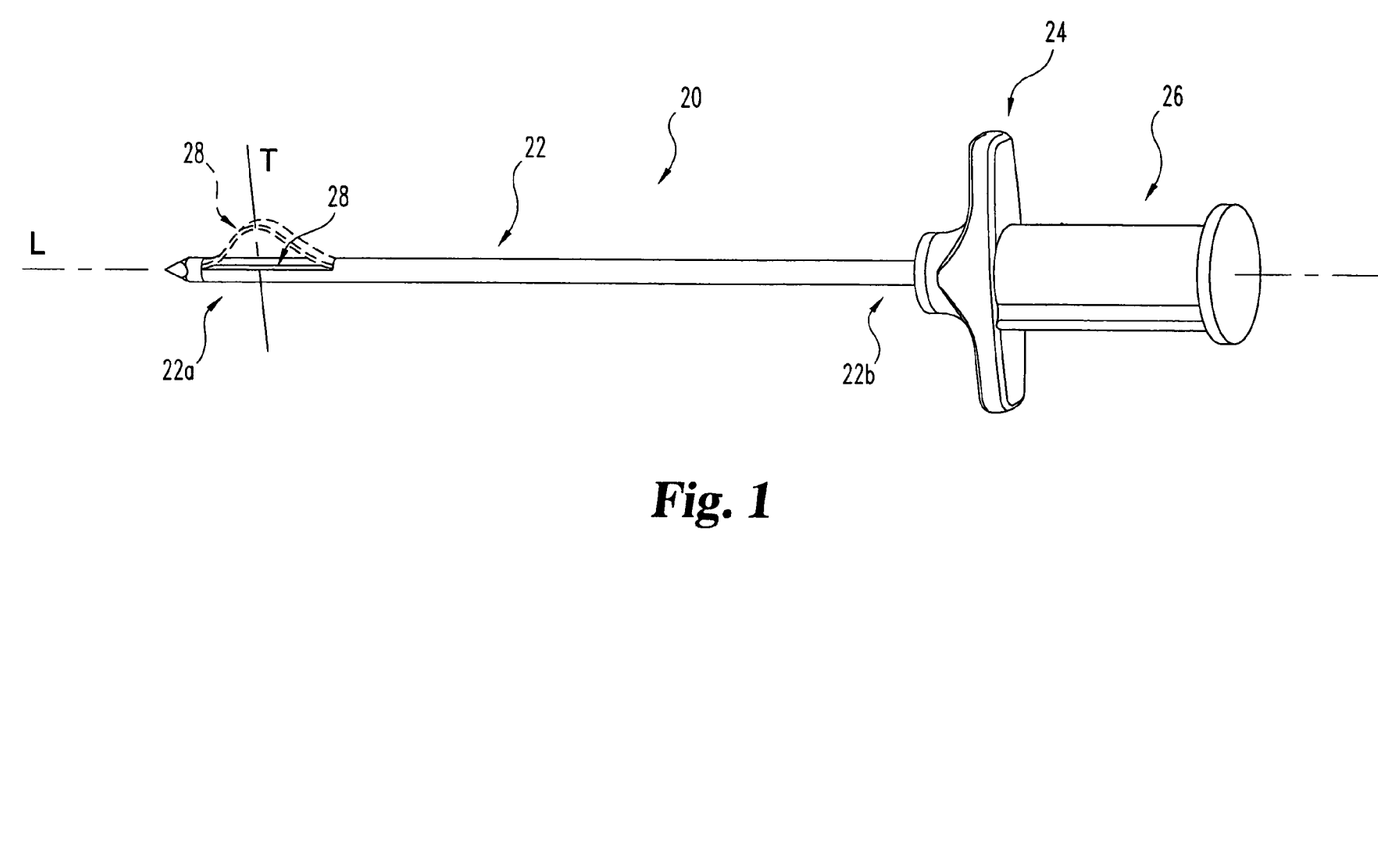
FIG. 1 is a perspective view of a surgical instrument according to one form of the present invention.

Referring to FIG. 1, shown therein is an instrument 20 for treatment of the spine according to one form of the present invention. The instrument 20 is particularly useful for placement adjacent a spinal structure to selectively displace at least a portion of the spinal structure. In one embodiment of the invention, the spinal structure is a vertebral body. In a preferred embodiment of the invention, the instrument 20 is used in intrabody applications such as, for example, a vertebral plasty procedure to compact cancellous bone tissue or bone marrow within the vertebral body and/or to reduce a compression fracture of the vertebral body.

However, it should also be understood that the instrument 20 may be used in other applications as well, such as interbody applications to distract an intervertebral space between adjacent vertebral bodies and/or to manipulate a structure positioned within the intervertebral space. It should further be understood that in other embodiments of the invention, the spinal structure may be comprised of a spinal implant such as, for example, a cage device, a spacer, an artificial disc, or any other structure used in association with treatment of the spine. Additionally, although the instrument 20 is illustrated and described in the context of treatment of a human spine, it should be understood that the instrument 20 may also be used to treat other animals. It should further be understood that the instrument 20 may be used in association with applications outside of the spinal field such as, for example, to treat other types of bony structures.

In one embodiment of the invention, the instrument 20 is designed for planned disposable upon use in association with a limited number of surgical procedures. In a specific embodiment, the instrument 20 is designed for a single use in association with a single surgical procedure. In instances where the instrument 20 is designed for a single use, immediate disposal eliminates the requirements and costs associated with cleaning, sterilizing, repackaging, and/or storing the instrument 20 for repeat use. However, it should be understood that the instrument 20 may be designed for use in association with multiple surgical procedures or may be designed to have a predetermined life span for use in association with a predetermined number of spinal surgeries after which the instrument 20 is subjected to disposal.

The instrument 20 is generally comprised of an elongate member 22, a handle portion 24, an actuator mechanism 26, and a deformable portion 28 that is selectively transitionable between an initial configuration (shown in solid lines) and a deformed configuration (shown in phantom lines). As used herein, the term "initial configuration" is broadly defined to encompass any structural configuration that is suitable for placement adjacent a spinal structure, and the term "deformed configuration" is broadly defined to encompass any structural configuration that is suitable for displacement of at least a portion of the spinal structure. As discussed above, in one embodiment of the invention, the spinal structure is a vertebral body, and displacement of the vertebral body could be associated with either intrabody or interbody applications.

The elongate member 22 extends generally along a longitudinal axis L and has a distal portion 22a and a proximal portion 22b. Although the illustrated embodiment depicts the elongate member 22 as having a generally linear, unitary configuration, it should be understood that elongate member 22 may take on other configurations such as, for example, a curvilinear configuration or a hinged configuration. The handle portion 24 aids in the manipulation and handling of the instrument 20 and also includes a mechanism for connecting to a material delivery system, the detail of which will be discussed below. The actuator mechanism 26 serves to transition the deformable portion 28 between the initial and deformed configurations. The deformable portion 28 is located adjacent the distal portion 22a of the elongate member 22 and outwardly expands along a transverse axis T in response to a mechanically induced force that is provided via selective actuation of the actuator mechanism 26.

Figure 2:
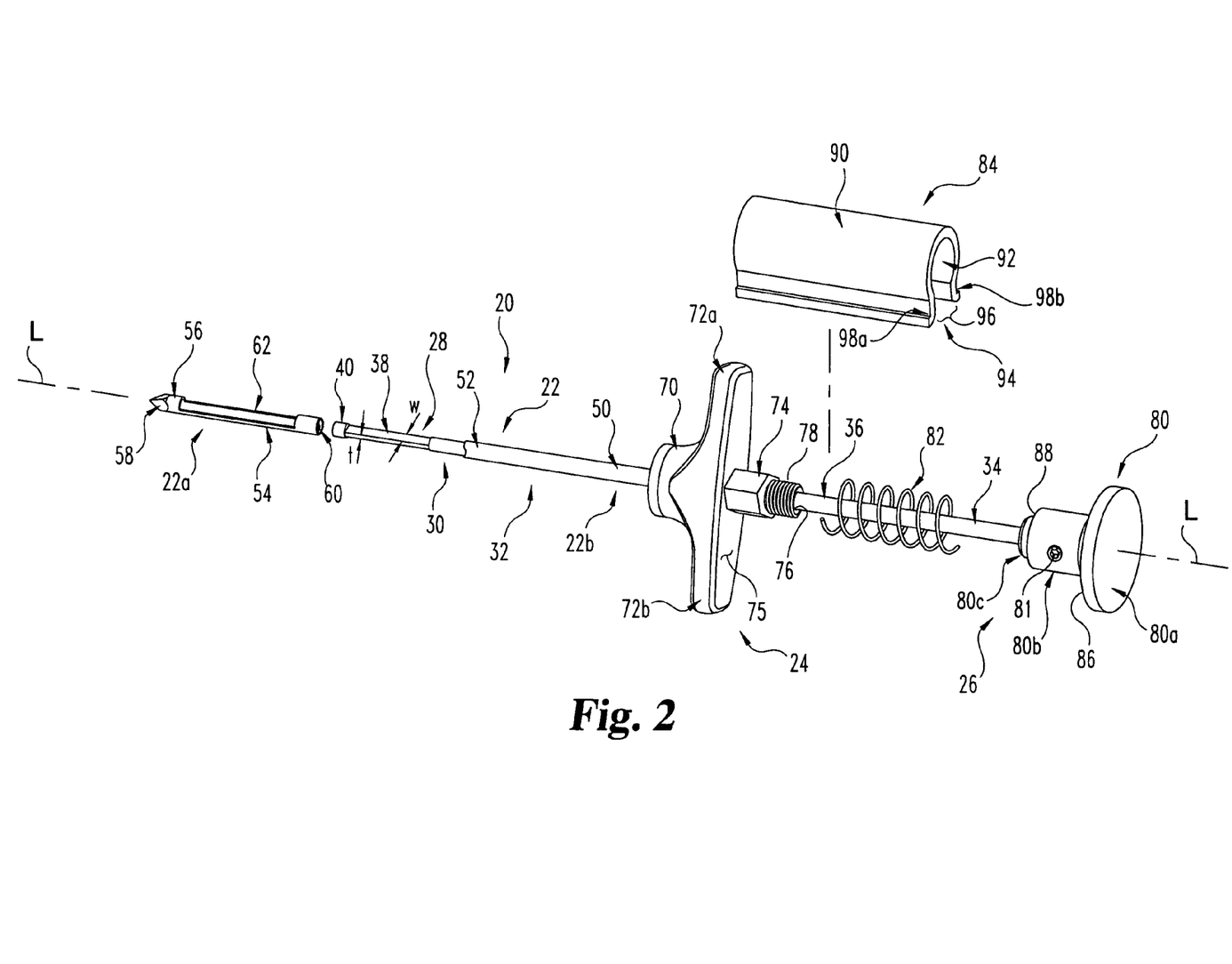
FIG. 2 is an exploded perspective view of the surgical instrument illustrated in FIG. 1.

Referring to FIG. 2, shown therein is an exploded view of the instrument 20 which illustrates additional elements and features associated with the elongate member 22, the handled portion 24, the actuator mechanism 26 and the deformable portion 28. Each of these components will now be discussed in greater detail.

In one embodiment of the invention, the elongate member 22 is generally comprised of an inner rod member 30 and an outer sleeve member 32. The inner rod 30 includes a proximal end portion 34, a main body portion 36, a deformable distal portion 38 (comprising the deformable portion 28), and a distal end portion 40. In one embodiment, the inner rod 30 is formed as a single-piece, unitary structure. However, it should be understood that portions of the inner rod 30 (such as the deformable portion 38 and/or the distal end portion 40) could be formed separately and coupled together by any known method such as by fastening, welding or adhesion.

In the illustrated embodiment, the proximal end portion 34, the main body portion 36 and the distal end portion 40 have a generally circular outer cross section that substantially corresponds to the inner cross section of the outer sleeve 32. However, it should be understood that other shapes and configurations are also contemplated as falling within the scope of the invention including, for example, elliptical, square, rectangular, hexagonal, or other arcuate or polygonal configurations. In the illustrated embodiment, the deformable portion 38 comprises a relatively thin, flexible strip of material extending generally along the longitudinal axis L. In a specific embodiment, the deformable strip 38 comprises a generally flat, spring-like element to facilitate transitioning between a relatively straight initial configuration and an outwardly deformed or buckled configuration. However, it should be understood that other suitable configurations of the deformable strip 38 are also contemplated to facilitate transitioning between an initial configuration and an outwardly deformed configuration.

The inner rod 30 is preferably formed of a medical grade material such as, for example, titanium or stainless steel. However, it should be understood that the inner rod 30 may be formed of other suitable medical grade materials. For example, in one embodiment, the deformable strip 38 may be formed of a flexible material that is capable of facilitating elastic deformation from the initial configuration toward the deformed configuration and reformation back toward the initial configuration. In a specific embodiment, at least the deformable strip 38 is formed of a thin metallic material such as titanium or stainless steel, an elastomeric material, a polymeric material, a rubber material, a composite material, or any other suitable flexible material to facilitate transitioning of the deformable strip 38 between the initial and deformed configurations. In another specific embodiment, at least the deformable strip 38 may be formed of a shape-memory material exhibiting superelastic characteristics to facilitate transitioning of the deformable strip 38 from the initial configuration to the deformed configurations and reformation back toward the initial configuration. For example, at least the deformable strip 38 may be formed of a shape-memory alloy ("SMA") such as, for example, Nitinol. Further details regarding the superelastic phenomena associated with an SMA material and the characteristics and behavior associated with stress-induced martensite are disclosed in U.S. patent application Ser. No. 09/928,949 to Foley et al., the contents of which are hereby incorporated by reference in their entirety.

As should be appreciated, the width, thickness, shape and/or cross section of the deformable strip 38 have an effect on the deformation characteristics and each provide a degree of control over the outward deformation/buckling of the deformable strip 38. Although the deformable strip 38 is illustrated as having a having a generally rectangular axial cross section defining a substantially uniform width w, it should be understood that the deformable strip 38 may define a non-uniform width w. For example, in an alternative embodiment, the deformable portion may define one or more cut-ins or grooves along its axial length. In a specific embodiment, the deformable strip 38 may be configured to have an hour-glass configuration to provide predetermined deformation characteristics associated with outward expansion of the deformable strip 38 along the transverse axis T. As should be appreciated, segments of the deformable strip 38 having a reduced width w would tend to provide less resistance to bending and serve as flexion points to facilitate outward deformation/buckling adjacent the areas of reduced width. Additionally, although the deformable strip 38 is illustrated as having a having a substantially uniform thickness t, it should be understood that the deformable strip 38 may define a non-uniform thickness t to provide predetermined deformation characteristics associated with outward expansion of the deformable strip 38 along the transverse axis T. As should be appreciated, segments of the deformable portion 38 having a reduced thickness t would tend to provide less resistance to bending and would thereby facilitate outward buckling adjacent the areas of reduced thickness.

In the illustrated embodiment of the invention, the inner rod 30 includes a single deformable strip 38 extending along the longitudinal axis L which is configured to outwardly deform/buckle in a single direction along the transverse axis T so as to provide controlled unidirectional expansion. However, it should be understood that in other embodiments of the invention, the inner rod 30 may include two or more deformable strips of material 38 extending along the longitudinal axis L which are configured to outwardly deform/buckle in multiple directions. In a specific embodiment, such outward deformation of the multiple strips of material would be limited to expansion along the transverse axis T so as to provide controlled uniaxial expansion.

The outer sleeve 32 generally includes a proximal end portion 50, a main body portion 52, a distal portion 54, and a distal end portion 56. In the illustrated embodiment, the proximal end portion 50 of the sleeve 32 extends axially from the handle portion 24 and the distal end portion 56 defines a pointed tip or trocar 58 to facilitate insertion into and/or through vertebral tissue. However, other configurations of the distal end portion 56 are also contemplated such as, for example, configurations defining a blunt or rounded tip to provide non-traumatic passage through vertebral tissue. The outer sleeve 32 is preferably formed of a substantially rigid medical grade material such as, for example, titanium or stainless steel. However, it should be understood that the outer sleeve 32 may be formed of other suitable medical grade materials.

In the illustrated embodiment of the invention, the outer sleeve 32 has a tubular configuration defining an axial cannula passage 60 extending generally along the longitudinal axis L and sized to slidably receive the inner rod 30 therein, the purpose of which will be discussed below. In one embodiment, the cannula passage 60 has a generally circular inner cross section substantially corresponding to the outer cross section of the main body portion 36 and distal end portion 40 of the inner rod 30. However, it should be understood that other shapes and configurations are also contemplated as falling within the scope of the invention including, for example, elliptical, square, rectangular, hexagonal or other arcuate or polygonal configurations. Additionally, although the outer sleeve 32 is illustrated as being formed as a single-piece, unitary structure, it should be understood that the distal end portion 56 could be formed separately from the remainder of sleeve 32 and coupled together by any known method such as by fastening, welding or adhesion.

In the illustrated embodiment of the invention, the distal portion 54 of the outer sleeve 32 defines a slotted opening 62 extending transversely through the sidewall of the sleeve 32 and communicating with the axial cannula passage 60. The slotted opening 62 is sized and shaped to receive the deformable portion 38 of the inner rod 30 therethrough when transitioned to the outwardly deformed configuration. Although the outer sleeve 32 is illustrated as including a single slotted opening 62, it should be understood that the outer sleeve 32 may define any number of slotted openings for receiving a corresponding number of deformable portions associated with the inner rod 30.

As discussed above, the handle portion 24 aids in the manipulation and handling of the instrument 20 and also includes a mechanism for connecting to a material delivery system. In one embodiment, the handle portion 24 is generally comprised of a base portion 70, a pair of lateral extensions 72a, 72b extending outwardly from the base portion 70, and a connector portion 74 extending proximally from the base portion 70 in an axial direction. The handle portion 24 also includes an axial passage 76 extending through the base portion 70 and the connector portion 74, the purpose of which will be discussed below.

The outer sleeve 32 extends distally from the base portion 70 with the cannula passage 60 communicating with the axial passage 76 in the handle portion 24. The lateral extensions 72a, 72b extending from the base portion 70 provide the handle portion 24 with a T-handle arrangement to aid the surgeon in grasping and manipulating the instrument 20. However, it should be understood that other types and configurations of handles are also contemplate for use in association with the instrument 10, an example of which will be discussed below in association with another embodiment of a surgical instrument 120.

Figure 5:
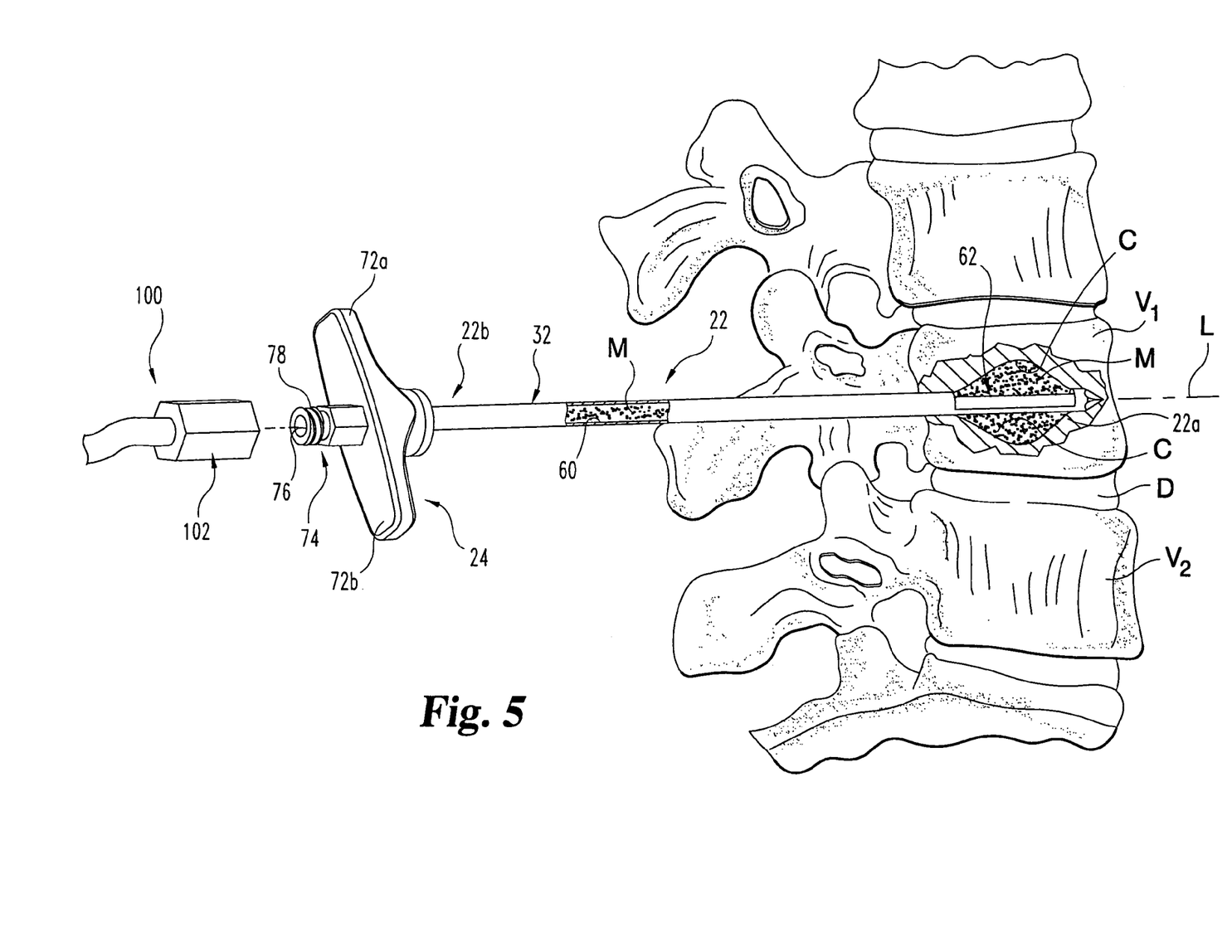
FIG. 5 is the surgical instrument illustrated in FIG. 1, as shown in a delivery configuration for conveying a filling material into the cavity formed within the vertebral body.

The connector portion 74 is configured for attachment to a system 100 (FIG. 5) for delivering material through the instrument 20 via the axial passage 76 and the cannula passage 60 and into a vertebral cavity, the details of which will be discussed below. In the illustrated embodiment, the connector portion 74 is a lure-type fitting defining external threads 78 adapted for threading engagement with an internally threaded connector element 102 of the material delivery system 100 (FIG. 5). However, it should be understood that other types and configurations of connector elements suitable for engagement with a material delivery system are also contemplated as falling within the scope of the invention such as, for example, a bayonet-type fitting, a quick-disconnect fitting, or any other suitable connection arrangement.

As discussed above, the actuator mechanism 26 serves to selectively transition the deformable strip portion 38 between the initial and deformed configurations to outwardly expand the deformable strip portion 38 along the transverse axis T in response to a mechanically induced force provided via selective actuation of the actuator mechanism 26. In one embodiment of the invention, the actuator mechanism 26 is generally comprised of an actuator button 80, a biasing member 82 and a retaining element 84. Although a specific embodiment of the actuator mechanism 26 has been illustrated and described herein, it should be understood that the use of other types and configurations of actuator mechanisms are also contemplated as would occur to one of skill in the art. For example, the actuator mechanisms illustrated and describe in U.S. patent application Ser. No. 09/928,949 to Foley et al. or any other suitable mechanism capable of selectively transitioning the deformable strip portion 38 between the initial and deformed configurations may also be used in association with the present invention. It should further be understood that in an alternative form of the invention, the inner rod 30 may be manually engaged by the surgeon, thereby eliminating the need for a separate actuator mechanism 26.

In one embodiment, the actuator button 80 includes an engaging portion 80a, an intermediate portion 80b, and a spring retaining portion 80c. The intermediate portion 80b has an outer cross section that is somewhat smaller than an outer cross section of the engaging portion 80a so as to define an axially-facing shoulder 86. Similarly, the spring retaining portion 80c has an outer cross section that is somewhat smaller than an outer cross section of the intermediate portion 80b so as to define an axially-facing shoulder 88. However, it should be understood that other types and configurations of actuator buttons are also contemplated for use in association with the present invention. The actuator rod 30 extends distally from the actuator button 80. In one embodiment, the proximal portion 34 of the actuator rod 30 is positioned within an axial passage (not shown) extending at least partially through the actuator button 80, with the actuator rod 30 attached to the actuator button 80 via a setscrew 81 or by any other suitable method of attachment.

In the illustrated embodiment of the invention, the biasing member 82 is configured as a coil spring. However, it should be understood that other types and configuration of biasing members are also contemplated as would occur to one of ordinary skill in the art. The coil spring 82 extends about the proximal portion 34 of the actuator rod 30. The distal portion of the spring 82 is positioned about the connector portion 74 of the handle 24 and abuts an axially facing surface 75 of the handle 24. The proximal portion of the spring 82 is positioned about the spring retaining portion 80c of the actuator button 80 and abuts the axial shoulder 88. As should be appreciated, the connector portion 74 and the spring retaining portion 80c aid in maintaining the spring 82 in the appropriate position and orientation relative to the handle portion 24 and the actuator button 80.

Figure 4:
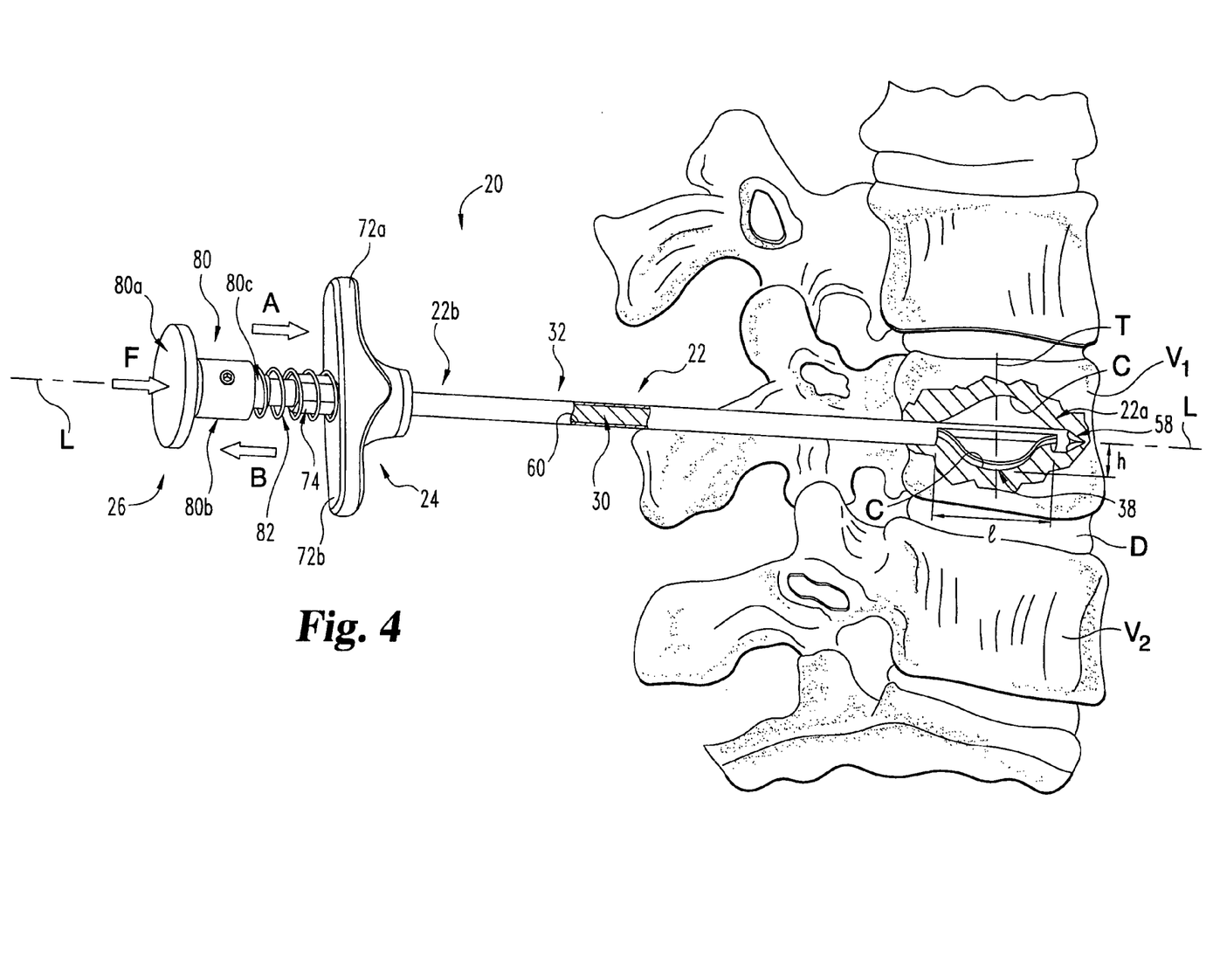
FIG. 4 is the surgical instrument illustrated in FIG. 1, as shown in an expanded configuration for forming a cavity within the vertebral body.

As illustrated in FIG. 4, exertion of an axial force F onto the engaging portion 80a of the actuator button 80 correspondingly exerts an axial force onto the actuator rod 30, which in turn axially displaces the actuator rod 30 in the direction of arrow A. As should be appreciated, the axial force F may be easily and conveniently provided via grasping of the instrument 20 with fingers wrapped about the lateral extension 72a, 72b of the handle 24 and with the palm positioned on the engaging portion 80a of the actuator button 80. The axial force F is thereby generated by depressing the actuator button 80 via the surgeon's palm. In this manner, the motion required to generate the axial force F is similar to the motion required to operate a syringe. As should also be appreciated, axial displacement of the actuator button 80 in the direction of arrow A correspondingly compresses the coil spring 82 between the handle 24 and the actuator button 80, the purpose of which will be discussed below.

Displacement of the actuator rod 30 in the direction of arrow A results in axial compression of the deformable strip portion 38 via opposing forces exerted onto the strip portion 38 by the movable main body portion 36 and the stationary distal end portion 40 of the actuator rod 30. The axial compression force exerted onto the strip portion 38 in turn causes the strip portion 38 to outwardly expand or buckle/bow along the transverse axis T. Outward expansion of the strip portion 38 causes the strip portion 38 to project through the transverse opening 62 in the outer sleeve 32. As should be appreciated, the degree of outward expansion of the strip portion 38 and the magnitude of the expansion force generated along the transverse axis T can be selectively and accurately controlled by varying the amount of axial force F exerted onto the actuator button 80. In other words, the amount of axial force F exerted onto the actuator button 80 by the surgeon is proportional to the degree of outward expansion and the magnitude of the expansion force associated with the strip portion 38.

Upon removal of the axial force F from the actuator button 80 via loosening of the surgeon's grip on the engaging portion 80a and the lateral extensions 72a, 72b, the biasing force exerted by the compressed coil spring 82 onto the actuator button 80 will correspondingly displace the actuator button 80 and the actuator rod 30 in the direction of arrow B. Displacement of the actuator rod 30 in the direction of arrow B results in removal of the axial compression force on the strip portion 38, which in turn results in reformation of the strip portion 38 from the outwardly deformed configuration illustrated in FIG. 4 back toward the initial configuration illustrated in FIG. 1.

Referring once again to FIG. 2, in one embodiment of the invention, the retaining element 84 is configured to selectively retain the actuator button 80 and the actuator rod 30 in a non-actuated position to avoid unintentional deployment or transitioning of the deformable strip portion 38 toward the outwardly expanded configuration. In the illustrated embodiment, the retaining element 84 has a clip-like configuration defining a horseshoe shape. However, other shapes and configurations of the retaining elements suitable for selectively maintaining the actuator button 80 and the actuator rod 30 in a non-actuated position are also contemplated as falling within the scope of the present invention.

In the illustrated embodiment, the retaining element 84 has a generally cylindrical sidewall 90 defining an axial passage 92 therethrough, and an axial slot 94 extending the length of the sidewall 90 so as to define a transverse opening 96 communicating with the axial passage 92. A pair of extension portions or flanges 98a, 98b extend from the cylindrical sidewall 90 in an outwardly tapering manner adjacent the transverse opening 96. The transverse opening 96 has a minimum opening width that is slightly less than the outer diameter of the intermediate portion 80*b* of the actuator button 80. Additionally, the retaining element 84 has a length that is substantially equal to the distance between the axially-facing surface 75 of the handle 24 and the axially-facing shoulder 86 of the actuator button 80.

As should be appreciated, the retaining element 84 is engagable with the remainder of the instrument 20 by aligning the transverse opening 96 with the proximal portion 34 of the actuator rod 30 and transversely displacing the retaining element 84 to a position between the handle 24 and the actuator button 80. The outwardly tapered extension portions 98*a*, 98*b* of the retaining element 84 serve to guide the proximal portion 34 of the actuator rod and the intermediate potion 80*b* of the actuator button into the axial passage 92. As should also be appreciated, since the width of the transverse opening 96 is sized slightly less than the outer diameter of the intermediate portion 80*b*, the sidewall 90 of the retaining element 84 is slightly outwardly deformed to receive the intermediate portion 80*b* through the transverse opening 96. Once the intermediate portion 80*b* is positioned within the axial passage 92, the sidewall 90 snaps back into its undeformed condition, thereby selectively engaging the retaining element 84 to the actuator button 80. As should further be appreciated, positioning of the retaining element 84 between the axially-facing surface 75 of the handle 24 and the axially-facing shoulder 86 of the actuator button 80 selectively retains the actuator button 80 and the actuator rod 30 in a non-actuated or non-deployed position.

Having described the components and features associated with the instrument 20, reference will now be made to a method for using the instrument 20 in the treatment of a portion of the spine according to one form of the present invention. However, it should be understood that other uses of the instrument 20 are also contemplated as falling within the scope of the present invention.

Figure 3:
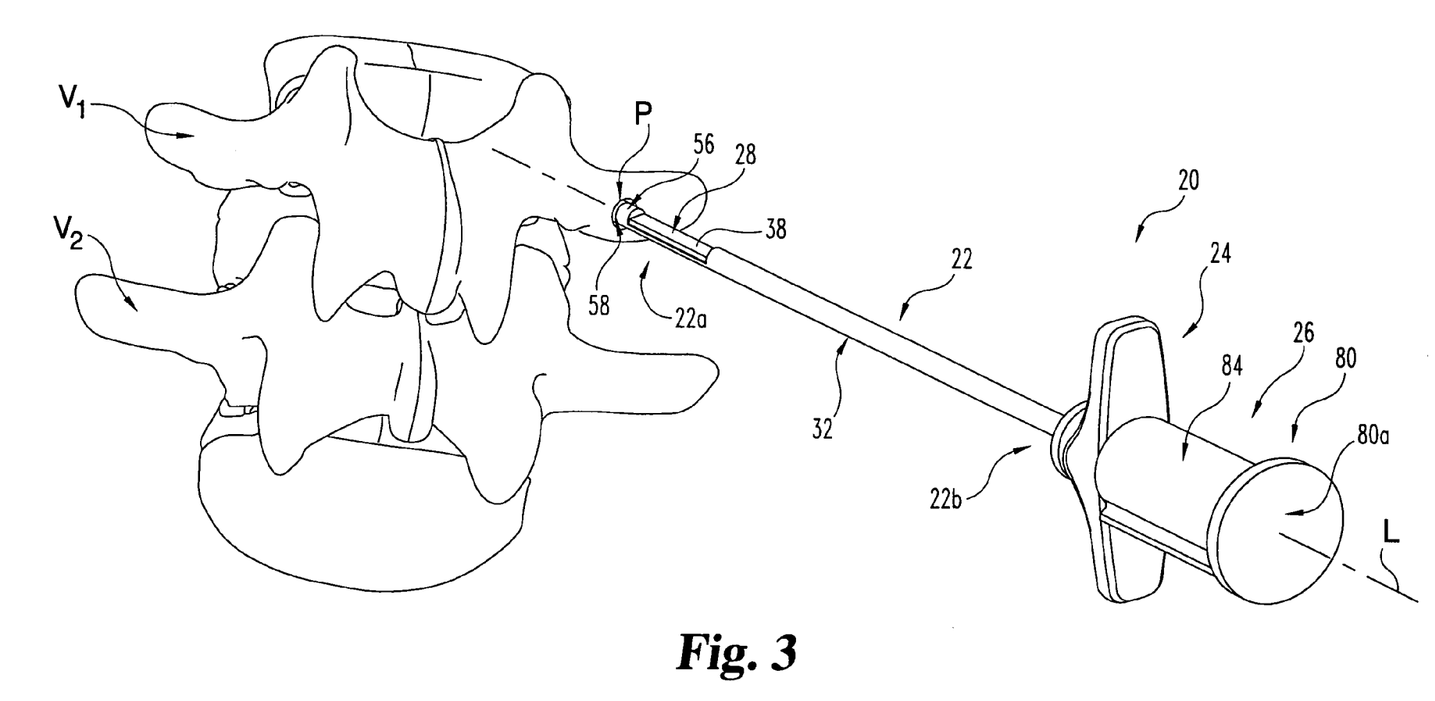
FIG. 3 is the surgical instrument illustrated in FIG. 1, as shown in an initial configuration for insertion of the distal portion of the instrument into a vertebral body.

Referring to FIG. 3, shown therein is a posterior view of a portion of a spinal column with the distal portion 22*a* of the instrument 20 being inserted through an access portal P formed through an outer wall of the vertebral body $V_1$. As discussed above, the retaining element 84 prevents unintentional deployment or transitioning of the distal portion 22*a* of the instrument 20 toward the outwardly expanded configuration during the initial introduction into the vertebral body $V_1$. As should also be appreciated, the distal portion 22*a* is inserted into the vertebral body $V_1$ while in the non-expanded initial configuration so as to define a minimal cross-sectional area to minimize the size of the access portal P. When in the non-expanded initial configuration, the distal end portion 22*a* has a relatively low profile to facilitate positioning adjacent a vertebral body. As used herein, positioning of the distal end portion 22*a* adjacent a vertebral body is meant to include positioning of the distal end portion 22*a* in proximity to a vertebral body, within a vertebral body or within a space between adjacent vertebral bodies. In one embodiment of the invention, the initial configuration of the distal end portion 22*a* is sized to pass through an access portal having a diameter between about 1 millimeter and about 10 millimeters. In a specific embodiment, the initial configuration of the distal end portion 22*a* is sized to pass through an access portal having a diameter of about 5 millimeters. However, other sizes are also contemplated as falling within the scope of the present invention.

In the illustrated embodiment, entry into the vertebral body $V_1$ is accomplished via a posterior approach and occurs through the pedicle region of the vertebral body $V_1$. Additionally, entry into the vertebral body $V_1$ could be either extrapedicular or trans-pedicular. However, it should be understood that in other embodiments of the invention, entry into the vertebral body $V_1$ may be accomplished via other surgical approaches such as, for example, an anterior or lateral approach, and could occur through other portions of the vertebral body. Additionally, as indicated above, the instrument 20 may also be used in interbody applications such as, for example, to distract a portion of the intervertbral space between the adjacent vertebral bodies $V_1$, $V_2$.

In one embodiment of the invention, access into the inner region of the vertebral body $V_1$ is accomplished by drilling a relatively small access portal P through an outer wall of the vertebral body $V_1$. The undeformed initial configuration of the distal end portion 22*a* of the instrument 20 is sized to pass through the small access portal P to gain access to the inner cancellous region of the vertebral body $V_1$. In this manner, insertion of the distal end portion 22*a* into the vertebral body $V_1$ is accomplished in a minimally invasive manner. In another embodiment of the invention, access into the inner region of the vertebral body $V_1$ may be accomplished by driving the pointed tip or trocar portion 58 of the instrument 20 into the vertebral body $V_1$ to form the access portal P via an impaction technique. As should be appreciated, with the retaining element 84 engaged between the handle 24 and the actuator button 80, an impaction force can be exerted onto the engaging portion 80*a* of the actuator button 80 to drive the distal portion 22*a* into the vertebral body $V_1$ while avoiding transitioning of the deformable strip portion 38 toward the outwardly expanded configuration.

Referring to FIG. 4, once the distal portion 22*a* is properly positioned adjacent or within the vertebral body $V_1$, the retaining element 84 is removed from the instrument 20 to allow for selective actuation or deployment of the instrument 20. Specifically, the distal portion 22*a* is transitioned from the initial insertion configuration illustrated in FIG. 3 to the outwardly deformed configuration illustrated in FIG. 4 via exertion of an axial force F onto the engaging portion 80*a* of the actuator button 80 to correspondingly displace the actuator rod 30 in the direction of arrow A. Axial displacement of the actuator rod 30 in the direction of arrow A in turn outwardly deforms the distal portion 22*a* along the transverse axis T. More specifically, axial compression of the deformable strip portion 38 cause the strip portion 38 to outwardly buckle or bow and project through the transverse opening 62 in the sleeve 32 so as to define a transverse projection or deformation along the transverse axis T. Since the illustrated embodiment of the instrument 20 defines a single transverse projection that extends in a single direction, formation of the transverse projection and the resulting displacement of the vertebral body is said to be unidirectional or directionally controlled.

It should be understood, however, that the instrument 20 may be configured to include multiple transverse projections. In another embodiment, the instrument 20 may be configured to include a pair of transverse projections extending in generally opposite directions and aligned along a common transverse axis T. In this alternative embodiment, formation of the transverse projections and the resulting displacement of the vertebral body would be described as uniaxial or axially controlled. Although not specifically illustrated herein, it should also be understood that the instrument 20 may also be configured to include multiple transverse projections positioned at various axial locations along the longitudinal axis L.

As discussed above, outward deformation of the distal portion 22*a* along the transverse axis T may be used to compact or compress cancellous bone against the inner cortical wall of the vertebral body to form an intervertebral cavity C therein. Compaction of the cancellous bone also exerts an outward force on the inner surface of the cortical wall adjacent the endplates and/or lateral walls of the vertebral body $V_1$, thereby making it possible to elevate or push broken and/or compressed bone back to or near its original prefracture condition or another desired condition. The deformed distal portion 22a may also bear directly against the inner surface of the cortical bone to reduce a compression fracture in the vertebral body $V_1$. As discussed above, other uses of the instrument 20 include, for example, distraction of the adjacent vertebral bodies to increase the height of the intervertebral disc space D and/or displacement a spinal implant or other structures used in association with treatment of the spine.

In one embodiment of the invention, the outwardly deformed configuration of the distal portion 22a has an overall height h along the transverse axis T (as measured from the longitudinal axis L) that falls within a range of about 3 millimeters to about 15 millimeters. In a specific embodiment, the outwardly deformed configuration of the distal portion 22a has an overall height h of about 7 millimeters. In another specific embodiment of the invention, the instrument 20 is capable of assuming a deformed configuration having an overall height h that is at least two to three times that of the height of the initial configuration. In another embodiment of the invention, the outwardly deformed configuration of the distal portion 22a has a length l (as measured along the longitudinal axis L) falling within a range of about 10 millimeters to about 40 millimeters. In a specific embodiment, the outwardly deformed configuration of the distal portion 22a has an overall length l of about 25 millimeters. Although ranges and specific sizes of the initial and deformed configurations of distal end potion 22a of the instrument 20 have been set forth above, it should be understood that such ranges and sizes are exemplary and do not limit the scope of the present invention in any manner whatsoever.

Following formation of the intervertebral cavity C in the vertebral body $V_1$, the distal end portion 22a of the instrument 20 is reformed back toward the initial configuration by displacing the actuator rod 30 in the direction of arrow B. As discussed above, upon the removal of the axial force F from the actuator button 80, the biasing force exerted by the compressed coil spring 82 onto the actuator button 80 will correspondingly displace the actuator button 80 and the actuator rod 30 in the direction of arrow B. Displacement of the actuator rod 30 in the direction of arrow B results in removal of the axial compression force on the strip portion 38, which in turn results in reformation of the distal portion 22a from the outwardly deformed configuration illustrated in FIG. 4 back toward the initial configuration illustrated in FIG. 1. As also discussed above, reformation of the distal portion 22a back toward the initial configuration may be facilitated by forming at least the strip portion 38 of a shape-memory material. Once transitioned back to the initial configuration, the distal portion 22a of the instrument 20 can be relocated to a different position and/or rotated to a different angular orientation. The instrument 20 can then be reactivated or redeployed by once again exerting an axial force F onto the actuator button 80 to outwardly deform the distal portion 22a along the transverse axis T to enlarge the intervertebral cavity C and/or to form another intervertebral cavity C within the vertebral body $V_1$.

Following formation of the intervertebral cavity or cavities C, the distal portion 22a of the instrument 20 is transitioned back toward the initial configuration illustrated in FIG. 1. In one embodiment of the invention, the instrument 20 is then removed from the vertebral body $V_1$. However, as illustrated in FIG. 5, in another embodiment of the invention the inner actuator rod 30 is removed from the outer sleeve 32 to define a hollow cannula passage 60 communicating between the transverse opening 62 and the axial passages 76 in the connector portion 74 of the handle 24. A material delivery system 100 may then be attached to the connector portion 74 to deliver a material M into the axial passage 76, through the hollow cannula 60, out the transverse opening 62 and into the vertebral cavity or cavities C. Although the illustrated embodiment of the invention depicts the outer sleeve 32 as defining a single transverse opening 62 for delivery of the material M into the vertebral cavity C, it should be understood that the sleeve 32 may define any number of transverse or axial openings for delivery of material M therethrough. It should also be understood that the outer sleeve 32 may define other types and configurations of delivery openings such as, for example, a plurality of substantially circular opening having a relatively smaller cross section than that of the transverse opening 62.

As shown in FIG. 5, the material M is delivered into the intervertebral cavity or cavities C to aid in the fixation and structural support of the vertebral body $V_1$. In one embodiment of the invention, the material M comprises a flowable material that is settable or curable following introduction into the cavity C. Once set to a hardened condition, the material M provides internal structural support to the vertebral body $V_1$, and more particularly provides structural support to the cortical bone of the vertebral body $V_1$. In a specific embodiment, the material M comprises a biocompatible filling material such as, for example, a bone cement or various types of synthetic bone material. In another specific embodiment, the material comprises methylmethacrylate cement. However, it should be understood that the material M may comprise other types of materials including, for example, a therapeutic substance to promote healing, a bone growth promoting substance, and/or one or more bone implant support structures.

Although not specifically illustrated in FIGS. 4 and 5, it should be understood that in a further embodiment of the invention, a cannula assembly may be used to provide minimally invasive access to the vertebral bodies $V_1$, $V_2$ and/or to the intervertebral disc space D. As should be appreciated, use of a cannula assembly would permit displacement of vertebral tissue via insertion and manipulation of the instrument 20 and other instrumentation or device through a single working channel. Further details regarding a cannula assembly suitable for use in association with the present invention are disclosed in U.S. patent application Ser. No. 09/692,932 to Foley et al. One feature associated with the use of a cannula assembly is the formation of a working channel having a relatively large cross section which permits the surgeon to introduce a wide variety of instruments or devices into the working channel as well as the simultaneous introduction of two or more instruments or devices into the working channel. Additionally, the relatively large cross section of the working channel would permit a wide range of motion of the instruments and devices. The cannula assembly may also include an endoscope assembly mounted to a proximal end portion thereof to provide remote visualization of the surgical site. One embodiment of an endoscope assembly suitable for use in association with the present invention is described in U.S. Pat. No. 6,152,871 to Foley et al., issued on Nov. 28, 2000, the contents of which are incorporated herein by reference.

Figure 6:
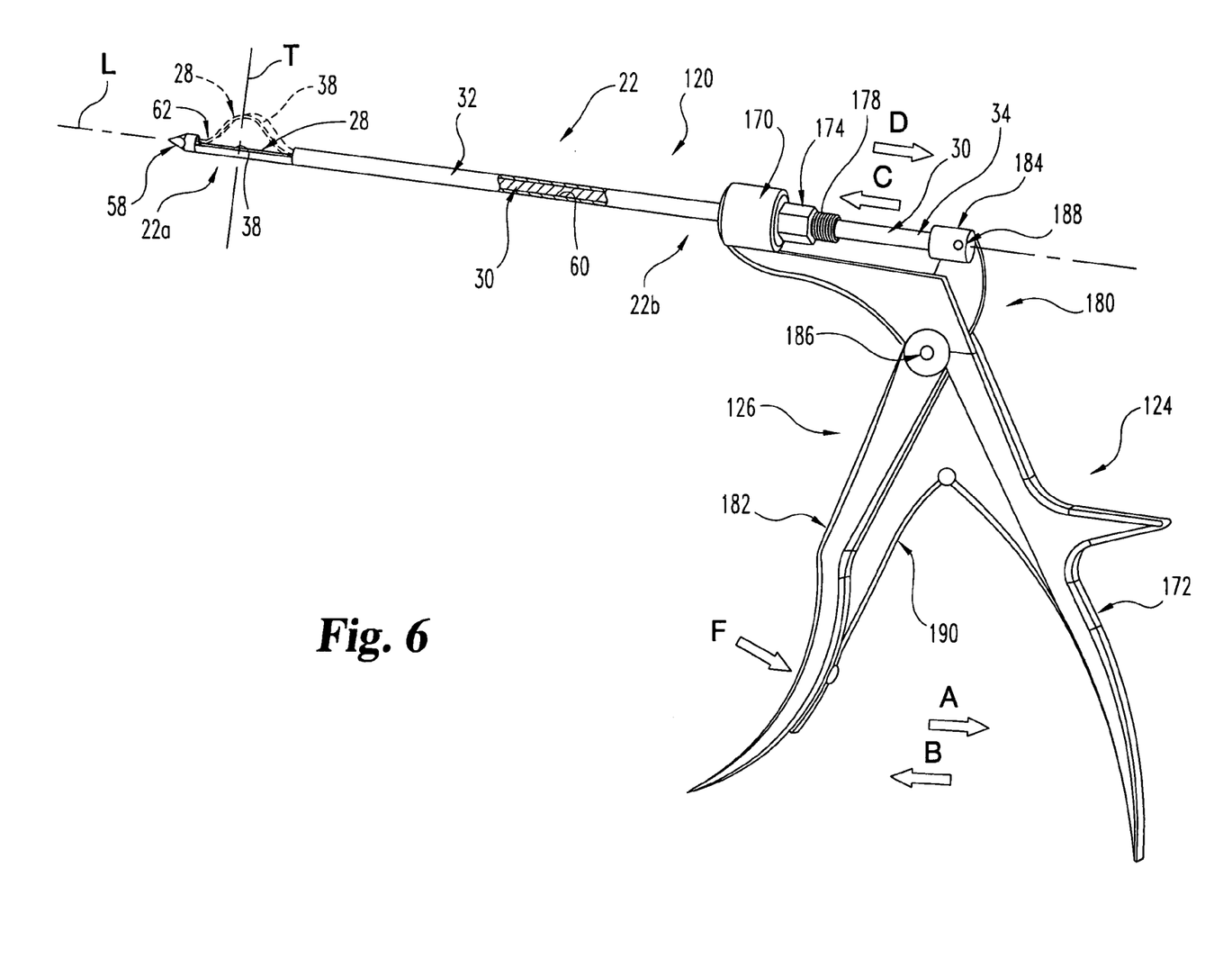
FIG. 6 is a perspective view of a surgical instrument according to another form of the present invention.

Referring to FIG. 6, shown therein is an instrument 120 for treatment of the spine according to another form of the present invention. The instrument 120 is used in association with applications such as those discussed above with regard to the instrument 20, and is particularly useful for placement adjacent a spinal structure to selectively displace at least a portion of the spinal structure. In many respects, the illustrated embodiment of the instrument 120 is structurally and functionally similar to the instrument 20 illustrated and described above. Accordingly, like elements and features are indicated and referred to using the same reference numerals.

Similar to the instrument 20, the instrument 120 is generally comprised of an elongate member 22, a handle portion 124, an actuator mechanism 126, and a deformable portion 28 that is selectively transitionable between an initial configuration (shown in solid lines) and a deformed configuration (shown in phantom lines). The elongate member 22 extends generally along a longitudinal axis L and has a distal portion 22a and a proximal portion 22b. The handle portion 124 aids in the manipulation and handling of the instrument 120 and also includes a mechanism for connecting to a material delivery system, the detail of which will be discussed below. The actuator mechanism 126 serves to transition the deformable portion 28 between the initial and deformed configurations. The deformable portion 28 is positioned adjacent the distal portion 22a of the elongate member 22 and outwardly expands along the transverse axis T in response to a mechanically induced force that is provided via selective actuation of the actuator mechanism 126.

In the illustrated embodiment, the handle portion 124 and the actuator mechanism 126 have a kerrison-type configuration. Specifically, the handle portion 124 is generally comprised of a base portion 170, a grip portion 172, and a connector portion 174. The handle portion 124 includes an axial passage (not shown) extending through the base portion 170 and the connector portion 174, with the outer sleeve 32 extending distally from the base portion 170. The cannula passage of the outer sleeve 32 communicates with the axial passage extending through the base portion 170 and the connector portion 174. The grip portion 172 aids the surgeon in grasping and manipulating the instrument 120. The connector portion 174 is configured for attachment to a system 100 (FIG. 5) for delivering a material M through the instrument 120 and into one or more vertebral cavities C. In the illustrated embodiment, the connector portion 174 comprises a lure-type fitting defining external threads 178 adapted for threading engagement with an internally threaded connector element 102 of the material delivery system 100 (FIG. 5). However, it should be understood that other types and configurations of connector elements suitable for engagement with a material delivery system are also contemplated as falling within the scope of the invention such as, for example, a bayonet-type fitting, a quick-disconnect fitting, or any other suitable connection arrangement.

As discussed above, the actuator mechanism 126 serves to selectively transition the deformable strip portion 38 between the initial and deformed configurations to outwardly expand the deformable strip portion 38 along the transverse axis T in response to a mechanically induced force provided via selective actuation of the actuator mechanism 126. In one embodiment of the invention, the actuator mechanism 126 is generally comprised of an actuator or trigger portion 180 and a biasing member 190. Although not specifically illustrated in FIG. 6, the actuator mechanism 126 may also include a retaining element configured to selectively retain the trigger portion 180 and the actuator rod 30 in a non-actuated position to avoid unintentional deployment or transitioning of the deformable strip portion 38 toward the outwardly expanded configuration. The trigger portion 180 generally includes a grip portion 182 and a coupler portion 184. The grip portion 182 is pivotally attached to the grip portion 172 of the handle 124 via a pivot pin 186 to allow for relative pivotal movement therebetween in the direction of arrows A and B. The grip portion 182 is pivotally attached to the coupler portion 184 via a pivot pin 188 to provide pivotal engagement between the proximal end 34 of the actuator rod 30 and the grip portion 182.

In the illustrated embodiment, the biasing member 190 is configured as a U-shaped strip-like spring element. However, it should be understood that other types and configuration of biasing members are also contemplated as would occur to one of ordinary skill in the art including, for example, a coil spring. The spring 190 is engaged between the grip portions 172, 182 and serves to bias the grip portions 172, 182 apart to maintain the instrument 120 in a non-actuated or non-deployed configuration. However, exertion of a force F onto the grip portion 182 causes the grip portion 182 to pivot in the direction of arrow A, which in turn exerts an axial force onto the proximal portion 34 of the actuator rod 30 to displace the actuator rod 30 in the direction of arrow C. Displacement of the actuator rod 30 in the direction of arrow C results in axial compression of the deformable strip portion 38, which in turn causes the strip portion 38 to outwardly expand or buckle/bow along the transverse axis T. As should be appreciated, the degree of outward expansion of the strip portion 38 and the magnitude of the expansion force generated along the transverse axis T can be selectively and accurately controlled by varying the amount of force F exerted onto the grip portion 182. In other words, the amount of force F exerted onto the grip portion 182 by the surgeon is proportional to the degree of outward expansion and the magnitude of the expansion force associated with the deformed strip portion 38.

In the illustrated embodiment, the force F exerted onto the grip portion 182 is provided via grasping of the instrument 120 with fingers wrapped about the grip portion 182 and with the palm and/or thumb positioned on the grip portion 172. The axial force F is thereby generated by squeezing the grip portion 182 toward the grip portion 172. As should be appreciated, pivotal movement of the grip portion 182 in the direction of arrow A correspondingly compresses the spring element 190 between the grip portions 172, 182. As should also be appreciated, upon removal of the force F via loosening of the surgeon's grip on the grip portion 182, the biasing force exerted by the compressed spring 190 will correspondingly displace the grip portion 182 in the direction of arrow B, which in turn displaces the actuator rod 30 in the direction of arrow D. Displacement of the actuator rod 30 in the direction of arrow D results in removal of the axial compression force on the strip portion 38, which in turn results in reformation of the strip portion 38 from the outwardly deformed configuration (as shown in phantom lines) back toward the initial configuration (as shown in sold lines).

Similar to the instrument 20 illustrated and described above, the instrument 120 is configured to allow for removal of the inner actuator rod 30 from the outer sleeve 32 to provide an axial passageway 60 for the delivery of a material M into the intervertebral cavity C formed within the vertebral body $V_1$. Specifically, following transitioning of the distal portion 22a of the instrument 120 back to the initial configuration, the actuator rod 30 is removed from the outer sleeve 32 to define a hollow cannula 60 communicating between the transverse slotted opening 62 and the connector portion 174. A material delivery system 100 (FIG. 5) may then be attached to the connector portion 174 to deliver a material M through the hollow cannula 60, out the transverse opening 62 and into the vertebral cavity C.

As should now be appreciated, in the illustrated embodiments of the invention, the instruments 20, 120 are capable of performing multiple functions associated with treatment of the spine. For example, the trocar 58 facilitates entry into and through vertebral tissue. Additionally, the deformable distal portion 22a, and more specifically the deformable strip portion 38, serves to reduce a vertebral fracture and/or to form one or more intervertebral cavities C with the vertebral body $V_1$. Further, upon the selective removal of the inner actuator rod 30, the outer sleeve 32 provides a hollow cannula 60 for delivering a material M into the intervertebral cavity C. As should be appreciated, the use of a single instrument to perform multiple functions associated with a spinal treatment procedure tends to simplify the surgical procedure, lessen the time required to perform the procedure, and/or reduce the costs and expenses compared to providing multiple surgical instruments to perform similar functions. Additionally, if the instrument 20, 120 is designed as a single use instrument, the cost associated with sterilizing the instrument 20, 120 for reuse are eliminated.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. Instrumentation for treatment of the spine, comprising: an elongate member extending along a longitudinal axis and including a flexible and elastically deformable distal portion having an initial configuration for placement within a spinal structure and an elastically deformed configuration wherein said distal portion is outwardly deformed, said elongate member comprising a cannula member and an actuator member, said actuator member being removably positioned within said cannula member and configured to transition said deformable distal portion from said initial configuration toward said elastically deformed configuration by imposition of an axial compression force onto said deformable distal portion, said actuator member being selectively removed from said cannula member to provide a passageway for delivery of a material into in the spinal structure; and wherein said cannula member defines a transverse opening communicating with said passageway, said elastically deformed configuration comprising a transverse projection extending through said transverse opening.

2. The instrumentation of claim 1, wherein said at least one transverse projection is arranged along a transverse axis such that outward deformation of said deformable distal portion is uniaxial along said transverse axis.

3. The instrumentation of claim 1, wherein said deformed configuration of said deformable distal portion comprises a single transverse projection such that outward deformation of said deformable distal portion is unidirectional.

4. The instrumentation of claim 1, further comprising a retaining element adapted to selectively prevent transitioning of said deformable distal portion from said initial configuration toward said deformed configuration.

5. The instrumentation of claim 1, wherein a distal end of said elongate member comprises a pointed trocar tip to facilitate introduction of said deformable distal portion into the spinal structure.

6. The instrumentation of claim 1, wherein said material comprises a flowable material.

7. The instrumentation of claim 6, wherein said material comprises a settable material providing internal support to a cavity formed in the spinal structure.

8. The instrumentation of claim 7, wherein said material comprises bone cement.

9. The instrumentation of claim 6, wherein said elongate member includes a connector portion defining a passage in communication with said passageway in said cannula member, said connector portion adapted for coupling with a material delivery system to inject said flowable material through said passageway in said cannula member and into a cavity in the spinal structure.

10. The instrumentation of claim 9, wherein said connector portion comprises a luer-type fitting.

11. The instrumentation of claim 9, wherein said connector portion comprises a threaded fitting adapted for threading engagement with said material delivery system.

12. The instrumentation of claim 1, wherein said axial compression force is provided by axial displacement of said actuator member relative to said deformable distal portion.

13. The instrumentation of claim 1, wherein said imposition of said axial compression force onto said deformable distal portion results in axial compression of said deformable distal portion to outwardly buckle said deformable distal portion toward said elastically deformed configuration.

14. Instrumentation for treatment of the spine, comprising: an elongate member extending along a longitudinal axis and including a flexible and elastically deformable distal portion having an initial configuration for placement within a spinal structure and an elastically deformed configuration wherein said distal portion is outwardly deformed to define at least one transverse projection arranged along a transverse axis such that outward deformation of said deformable distal portion is uniaxial along said transverse axis, said outward deformation of said deformable distal portion being selectively controlled to generate a controlled magnitude of force against the spinal structure, said elongate member comprising a cannula member and an actuator member, said actuator member being removably positioned within said cannula member and configured to transition said deformable distal portion from said initial configuration toward said elastically deformed configuration, said actuator member being selectively removed from said cannula member to provide a passageway for delivery of a material into the spinal structure, wherein said cannula member defines a transverse opening communicating with said passageway, said elastically deformed configuration comprising a transverse projection extending through said transverse opening.

15. Instrumentation for treatment of the spine, comprising: an elongate member extending along a longitudinal axis and including a deformable distal portion having an initial configuration for placement within a spinal structure and a deformed configuration wherein said distal portion is outwardly deformed, said elongate member comprising a cannula member and an actuator member, said actuator member being removably positioned within said cannula member and configured to transition said deformable distal portion from said initial configuration toward said deformed configuration, said actuator member being selectively removed from said cannula member to provide a passageway for delivery of a material into the spinal structure; and
  wherein relative displacement between said actuator member and said cannula member results in axial compression of said deformable distal end portion to transition said deformable distal end portion toward said deformed configuration; and wherein said cannula member defines a transverse opening communicating with said passageway, said deformed configuration comprising a transverse projection extending through said transverse opening.

16. The instrumentation of claim 15, further comprising an actuator mechanism coupled between said actuator member and said cannula member to regulate said relative displacement therebetween and to generate a controlled magnitude of force against the spinal structure.

17. The instrumentation of claim 15, further comprising a retaining element engaged between said actuator member and said cannula member to selectively prevent said relative displacement and transitioning of said deformable distal portion from said initial configuration toward said deformed configuration; and wherein disengagement of said retaining element from between said actuator member and said cannula member permits said relative linear displacement and transitioning of said deformable distal portion from said initial configuration toward said deformed configuration.

18. Instrumentation for treatment of the spine, comprising:

an elongate member extending along a longitudinal axis and including a deformable distal portion having an initial configuration for placement within a spinal structure and a deformed configuration wherein said distal portion is outwardly deformed, said elongate member comprising a cannula member and an actuator member, said outward deformation of said deformable distal portion resulting from relative displacement between said actuator member and said cannula member, said actuator member being removably positioned within said cannula member and configured to transition said deformable distal portion from said initial configuration toward said deformed configuration, said actuator member being selectively removed from said cannula member to provide a passageway for delivery of a material into the spinal structure;

a handle attached to said cannula member and an actuator button attached to said actuator member; and a retaining element positioned between said handle and said actuator button to selectively prevent said relative displacement and said transitioning of said deformable distal portion from said initial configuration toward said deformed; and wherein disengagement of said retaining element from between said handle and said actuator button permits said relative displacement and said transitioning of said deformable distal portion from said initial configuration toward said deformed configuration.

19. Instrumentation for treatment of the spine, comprising:

an elongate member extending along a longitudinal axis and including a deformable distal portion having an initial configuration for placement within a spinal structure and a deformed configuration wherein said distal portion is outwardly deformed, said elongate member comprising a cannula member and an actuator member, said actuator member being removably positioned within said cannula member and configured to transition said deformable distal portion from said initial configuration toward said deformed configuration by imposition of an axial compression force onto said deformable distal portion, said actuator member being selectively removed from said cannula member to provide a passageway for delivery of a material into the spinal structure; and wherein said cannula member defines a transverse opening communicating with said passageway, said actuator member including a deformable element disposed adjacent said transverse opening; and wherein said deformable configuration comprises an outward deformation of said deformable element to form a transverse projection extending through said transverse opening in said cannula member.

20. The instrumentation of claim 19, wherein said deformable element has a substantially flat configuration when in said initial configuration and an arcuate configuration when transitioned to said deformed configuration.

21. The instrumentation of claim 19, wherein said deformable element comprises a flexible strip of material to facilitate transitioning to said deformed configuration and formation of said transverse projection.

22. The instrumentation of claim 19, wherein said deformable element comprises a flat spring; and wherein axial compression of said flat spring results in transitioning to said deformed configuration and formation of said transverse projection.

23. The instrumentation of claim 19, wherein said axial compression force is provided by axial displacement of said actuator member relative to said deformable distal portion.

24. The instrumentation of claim 19, wherein said imposition of said axial compression force onto said deformable distal portion results in axial compression of said deformable distal portion to outwardly buckle said deformable distal portion toward said deformed configuration.

25. Instrumentation for treatment of the spine, comprising:

a cannula member extending along a longitudinal axis and including a distal portion, said cannula member defining an axial passage and a transverse opening positioned adjacent said distal portion and communicating with said axial passage; and an actuator member removably positioned within said axial passage of said cannula member and including a deformable portion positioned adjacent said transverse opening, said deformable portion being transitionable between an initial configuration for placement within a spinal structure and a deformed configuration defining a transverse projection extending through said transverse opening in said cannula member, said transitioning of said deformable portion is selectively controlled to generate a controlled magnitude of force against the spinal structure; and wherein said actuator member is selectively removed from said cannula member to allow for delivery of a material through said axial passage and into the spinal structure.

26. Instrumentation for treatment of the spine, comprising:

a cannula member extending along a longitudinal axis and including a distal portion, said cannula member defining an axial passage and a transverse opening positioned adjacent said distal portion and communicating with said axial passage; and an actuator member removably positioned within said axial passage of said cannula member and including a deformable portion positioned adjacent said transverse opening, said deformable portion being transitionable between an initial configuration for placement within a spinal structure and a deformed configuration defining a transverse projection extending through said transverse opening in said cannula member, wherein outward deformation of said deformable portion results from relative displacement between said actuator member and said cannula member; and an actuator mechanism coupled between said actuator member and said cannula member to regulate said relative displacement therebetween and generate a controlled magnitude of force against the spinal structure; and wherein said actuator member is selectively removed from said cannula member to allow for delivery of a material through said axial passage and into the spinal structure.

27. Instrumentation for treatment of the spine, comprising:

a cannula member extending along a longitudinal axis and including a distal portion, said cannula member defining an axial passage and a transverse opening positioned adjacent said distal portion and communicating with said axial passage; and an actuator member removably positioned within said axial passage of said cannula member and including a deformable portion positioned adjacent said transverse opening, said deformable portion being transitionable between an initial configuration generally aligned with said transverse opening for placement within a spinal structure and a deformed configuration defining a transverse projection extending through said transverse opening in said cannula member, said deformable portion transitioned from said initial configuration to said deformed configuration by imposition of a compression force onto said deformable portion; and wherein said actuator member is selectively removed from said cannula member to allow for delivery of a material through said axial passage and into the spinal structure.

28. The instrumentation of claim 27, wherein said deformable portion has a substantially flat configuration when in said initial configuration and an arcuate configuration when transitioned to said deformed configuration.

29. The instrumentation of claim 27, wherein said deformable portion comprises a flexible strip of material to facilitate transitioning to said deformed configuration and formation of said transverse projection.

30. The instrumentation of claim 27, wherein said deformable portion comprises a flexible strip of material; and
wherein axial compression of said flexible strip of material results in transitioning to said deformed configuration and formation of said transverse projection.

31. The instrumentation of claim 27, wherein outward deformation of said deformable portion results from relative displacement between said actuator member and said cannula member.

32. The instrumentation of claim 27, wherein a distal end of said cannula member comprises a pointed trocar tip to facilitate introduction into the spinal structure.

33. The instrumentation of claim 27, wherein said material comprises a flowable material.

34. The instrumentation of claim 33, wherein said material comprises a settable bone cement to provide internal support to a cavity formed in the spinal structure.

35. The instrumentation of claim 33, further comprising a connector member defining a passage in communication with said axial passage in said cannula member, said connector member adapted for coupling with a material delivery system to inject said flowable material through said axial passage and into a cavity in the spinal structure.

36. The instrumentation of claim 27, wherein said compression force is provided by axial displacement of said actuator member relative to said deformable portion.

37. The instrumentation of claim 27, wherein said imposition of said compression force onto said deformable portion results in axial compression of said deformable portion to outwardly buckle said deformable portion toward said deformed configuration.

38. The instrumentation of claim 27, wherein said imposition of said compression force onto said deformable portion comprises exertion of an axial force onto said deformable portion to transition said deformable portion toward said deformed configuration.

39. The instrumentation of claim 38, wherein said axial force is provided by axial displacement of said actuator member relative to said deformable portion.

40. The instrumentation of claim 27, wherein said deformable portion is formed of a flexible and elastically deformable material to facilitate transitioning to said deformed configuration and formation of said transverse projection.

41. Instrumentation for treatment of the spine, comprising:
an elongate member extending along a longitudinal axis and including a flexible and elastically deformable distal portion having an initial configuration for insertion into a spinal structure and a mechanically and elastically deformed configuration; and means for mechanically defining said distal portion from said initial configuration toward said mechanically and elastically deformed configuration by imposition of an axial compression force onto said deformable distal portion; and means for delivering a material through said elongate member and into the spinal structure; and wherein said elongate member defines a transverse opening communicating with said passageway, said mechanically and elastically deformed configuration comprising a transverse projection extending through said transverse opening.

42. The instrumentation of claim 41, further comprising means for selectively preventing transitioning of the deformable distal portion from the initial configuration toward the mechanically deformed configuration.

43. The instrumentation of claim 41, further comprising means for selectively controlling said imposition of said axial compression force onto said deformable distal portion to generate a controlled magnitude of force against the spinal structure.

44. The instrumentation of claim 41, wherein said axial compression force is provided by relative axial displacement of said deformable distal portion.

45. The instrumentation of claim 41, wherein said imposition of said axial compression force onto said deformable distal portion results in axial compression of said deformable distal portion to outwardly buckle said deformable distal portion toward said elastically deformed configuration.

46. The instrumentation of claim 41, further comprising means for coupling said means for delivering to said elongate member.

* * * * *

UNITED STATES PATENT AND TRADEMARK OFFICE
CERTIFICATE OF CORRECTION

PATENT NO. : 7,641,664 B2 Page 1 of 1
APPLICATION NO. : 10/778650
DATED : January 5, 2010
INVENTOR(S) : Paul J. Pagano It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 802 days.

Signed and Sealed this

Sixteenth Day of November, 2010

David J. Kappos
*Director of the United States Patent and Trademark Office*